United States Patent
Johnson

(10) Patent No.: US 7,625,884 B2
(45) Date of Patent: Dec. 1, 2009

(54) FORMULATIONS AND USES OF 2-HYDROXY-5-PHENYLAZOBENZOIC ACID DERIVATIVES

(75) Inventor: Lorin Johnson, Palo Alto, CA (US)

(73) Assignee: Salix Pharmaceuticals, Ltd, Morrisville, NC (US)

( * ) Notice: Subject to any disclaimer, the term of this patent is extended or adjusted under 35 U.S.C. 154(b) by 0 days.

(21) Appl. No.: 11/877,589

(22) Filed: Oct. 23, 2007

(65) Prior Publication Data
US 2008/0096849 A1    Apr. 24, 2008

Related U.S. Application Data

(60) Division of application No. 11/835,897, filed on Aug. 8, 2007, now Pat. No. 7,452,872, which is a continuation-in-part of application No. 11/592,854, filed on Nov. 3, 2006, and a continuation-in-part of application No. PCT/US2006/033255, filed on Aug. 24, 2006.

(60) Provisional application No. 60/711,300, filed on Aug. 24, 2005.

(51) Int. Cl.
A61K 31/655    (2006.01)
(52) U.S. Cl. .................. 514/149; 514/151; 514/158
(58) Field of Classification Search ............. 514/149, 514/151, 158
See application file for complete search history.

(56) References Cited

U.S. PATENT DOCUMENTS

| | | | |
|---|---|---|---|
| 5,196,205 A | 3/1993 | Borody et al. |
| 5,476,669 A | 12/1995 | Borody et al. |
| 5,498,608 A | 3/1996 | Johnson et al. |
| 5,519,014 A | 5/1996 | Borody et al. |
| 5,905,073 A | 5/1999 | Johnson et al. |
| 6,197,341 B1 | 3/2001 | Friess et al. |
| 6,277,836 B1 | 8/2001 | Borody et al. |
| 6,326,364 B1 | 12/2001 | Lin et al. |
| 6,407,128 B1 | 6/2002 | Scaife et al. |
| 6,426,338 B1 | 7/2002 | Borody et al. |
| 6,475,518 B1 | 11/2002 | Baumgart et al. |
| 6,551,632 B2 | 4/2003 | Borody et al. |
| 6,683,102 B2 | 1/2004 | Scaife et al. |

(Continued)

FOREIGN PATENT DOCUMENTS

EP    0 974 344 B1    1/2000

(Continued)

OTHER PUBLICATIONS

Guidance for Industry, USDA (Dec. 2002).*

(Continued)

*Primary Examiner*—Frederick Krass
*Assistant Examiner*—Benjamin Packard
(74) *Attorney, Agent, or Firm*—Edwards Angell Palmer & Dodge LLP; Peter F. Corless; Jonathan M Sparks

(57) ABSTRACT

A method of increasing the bioavailability of balsalazide by administration of an oral dosage form with food is provided, as well as an article of manufacture comprising an oral dosage form of balsalazide in a suitable container and associated with printed labeling which describes the increased bioavailability of the medication in the container when taken with food.

9 Claims, 2 Drawing Sheets

U.S. PATENT DOCUMENTS

2006/0223787 A1    10/2006    Devane et al.

FOREIGN PATENT DOCUMENTS

| WO | WO-95/18622 | 7/1995 |
|---|---|---|
| WO | WO-2004/012699 | 2/2004 |
| WO | WO-2005/030173 | 4/2005 |

OTHER PUBLICATIONS

Goebell H; Klotz U; Nehlsen B; Layer P, "Oroileal transit of slow release 5-aminosalicylic acid," Gut, (May 1993) vol. 34, No. 5, pp. 669-675.

Biotech Business, "Colazal "Food Effect" Application Granted FDA Approval," (Nov. 1, 2006) vol. 19, No. 11.

Schellekens R.C.A.; Stuurman F.E.; van der Weert F.H.J.; Kosterink, J.G.W.; Frijlink, H.W., "A novel dissolution method relevant to intestinal release behaviour and its application in the evaluation of modified release mesalazine products." European Journal of Pharmaceutical Sciences, (2007) vol. 30, No. 1, pp. 15-20.

De Vos, M., "Clinical pharmacokinetics of slow release mesalazine," Clinical Pharmacokinetics, (2000) vol. 39, No. 2, pp. 85-97.

Norlander, B.; Gotthard R.; Strom M., "Pharmacokinetics of a 5-aminosalicylic acid enteric-coated tablet and suppository dosage form," Alimentary Pharmacology and Therapeutics, (1989) vol. 3, No. 4, pp. 333-342.

Wilding, I R; Kenyon, C J; Hooper, G., "Gastrointestinal spread of oral prolonged-release mesalazine microgranules (Pentasa) dosed as either tablets or sachet," Alimentary pharmacology & therapeutics, (Feb. 2000) vol. 14, No. 2, pp. 163-169.

Layer, P. H.; Goebell, H.; Keller, J.; Dignass, A.; Klotz, U., "Delivery and fate of oral mesalamine microgranules within the human small intestine," Gastroenterology, (May 1995) vol. 108, No. 5, pp. 1427-1433.

Wadworth, A N; Fitton, A., "Olsalazine. A review of its pharmacodynamic and pharmacokinetic properties, and therapeutic potential in inflammatory bowel disease," Drugs, (Apr. 1991) vol. 41, No. 4, pp. 647-664.

Qureshi, Altamash I.; Cohen, Russell D., "Mesalamine delivery systems: do they really make much difference?" Advanced Drug Delivery Reviews (2005), 57(2), 281-302.

Norlander, B.; Gotthard, R.; Stroem, M., "Pharmacokinetics of a 5-aminosalicylic acid enteric-coated tablet and suppository dosage form," Alimentary Pharmacology and Therapeutics (1989), 3(4), 333-42.

Keller, J.; Goebell H.; Klotz, U.; Layer, P., [Release patterns of 5-aminosalicylic acid in human small intestine: Importance of galenic preparation], Medizinische Klinik, (May 15, 1998) vol. 93, No. 5, pp. 294-299. Language: German (English Abstract).

Godde, R. [Bioavailability in mesalazine therapy: Microcapsules to optimize concentrations in the bowel], Krankenhauspharmazie, (1996) vol. 17, No. 3, pp. 99-104. Language: German (English Abstract).

Yu, D.K.; Elvin, A.T.; Morrill, B.; Eichmeier, L.S.; Lanman, R.C.; Lanman, M.B.; Giesing, D.H.; "Effect of food coadministration on 5-aminosalicylic acid oral suspension bioavailaibility," Clin Pharmacol Ther. Jul. 1990; 48(1):26-33.

De Mey, C. and Meineke, I., "Prandial and diurnal effects on the absorption of orally administered enteric coated 5-aminosalicylic acid (5ASA)," Br J Clin Pharmacol. Feb. 1992; 33(2):179-82.

Ryde, E.M. and Ahnfelt, N.O., "The pharmacokinetics of olsalazine sodium in healthy volunteers after a single i.v. does and after oral doses with and without food," Eur J Clin Pharmacol. 1988;34(5):481-8.

Klotz, U., "Clinical pharmacokinetics of sulphasalazine, its metabolites and other prodrugs of 5-aminosalicylic acid," Clin Pharmacokinet. Jul.-Aug. 1985;10(4):285-302.

Lialda Package Insert.

Salix Study No. MPPK 1002. "Granulated Mesalamine Food Effect Pk."

Colazal Package Insert.

Pentasa Summary Basis for Approval.

Asacol Summary Basis for Approval.

NDA 20-610/S-014 pp. 3-11.

NDA 20-610/S014 Letter to Ms. Kompa, Director of Regulartory Affairs.

Colonic N-Acetylation of 5-Aminosalicylic Acid in Inflammatory Bowel Disease.

* cited by examiner

# FORMULATIONS AND USES OF 2-HYDROXY-5-PHENYLAZOBENZOIC ACID DERIVATIVES

RELATED APPLICATIONS

This application is a divisional of U.S. application Ser. No. 11/835,897, filed Aug. 8, 2007, which is a continuation-in-part of U.S. application Ser. No. 11/592,854, filed Nov. 3, 2006, which is hereby incorporated by reference in its entirety. U.S. application Ser. No. 11/835,897 is also a continuation-in-part of PCT Application No. PCT/US2006/033255, filed Aug. 24, 2006, which claims priority to U.S. Provisional Application Ser. No. 60/711,300, filed Aug. 24, 2005.

BACKGROUND

Balsalazide disodium is the drug substance of the reference branded drug, COLAZAL®. COLAZAL is indicated for the treatment of gastrointestinal diseases, for example mild to moderately active ulcerative colitis, radiation protosigmoiditis, and colon cancer (see WO 95/18622). Balsalazide is a colon-specific, non-steroidal, anti-inflammatory aminosalicylate derivative. Balsalazide is also a prodrug containing 5-ASA, linked to 4-amino benzoyl-β-alanine ("4-ABA") by a diazo bond. While 5-ASA is the active therapeutic moiety of balsalazide, it is rapidly converted to the metabolite N-acetyl-5-ASA (NASA) in the mucosa (Allgayer H, Ahnfelt N O, Kruis W et al Gastroenterology. 1989; 97:38-41). Approximately, 12% of the oral dose can be measured in the blood as this metabolite as compared to <2% of the oral dose of 5-ASA that is systemically absorbed (COLAZAL Package Insert, September 2006). NASA is known to be of lower anti-inflammatory activity in the colon (van Hogezand R A, van Hees P A, van Gorp J P, van Lier H J, Bakker J H, Double-blind comparison of 5-aminosalicylic acid and acetyl-5-aminosalicylic acid suppositories in subjects with idiopathic proctitis. Aliment Pharmacol Ther. 1988 February; 2(1):33-40), and is therefore thought to be less toxic when in the systemic circulation.

Pharmacokinetic studies have not previously been conducted to evaluate the effect of food on the pharmacokinetics of balsalazides, e.g., balsalazide. More bioavailability of the drug substance and less systemic adsorption has been sought to increase both speed of onset and amount of therapeutic effect.

Thus, there is a need in the art for dose regimens that decrease the systemic level of total mesalamine (5-ASA and NASA) and increase the systemic level of NASA at the expense of decreasing the level of 5-ASA (e.g., the ratio of NASA to 5-ASA) in the systemic circulation. There is also a need in the art for dose regimens that delay the transit of 5-ASA in the colon, as this will also result in an increase in contact time with the colonic mucosa, and increase efficacy of the drug.

SUMMARY

This invention relates to the use of balsalazide to treat, prevent, or ameliorate gastrointestinal disorders. More specifically, this invention relates to the use of balsalazide, to treat ulcerative colitis, radiation enteritis, irritable bowel syndrome and other non-inflammatory gastrointestinal (GI) conditions responding to mesalamine and balsalazide (U.S. Pat. Nos. 326,364; 6,551,632; 6,475,518; 6,426,338; 6,277,836; 5,519,014; 5,476,669; 5,196,205 and 6,645,530, which are hereby incorporated by reference). The invention also relates to the use of balsalazide to treat gastrointestinal disease, alone or in combination with other therapies.

The invention is due, in part, to the unexpected finding that administration of balsalazide with food increases both the bioavailability and decreases the systemic adsorption of 5-ASA via the oral dosage form in human subjects.

In one embodiment, the bioavailability of balsalazide is increased compared to administering balsalazide without food.

In one aspect, provided herein are methods of increasing the bioavailability of balsalazide comprising administering to a subject a therapeutically effective amount of balsalazide with food.

In one embodiment, the bioavailability of balsalazide is increased by decreasing the amount of metabolite in blood In one embodiment, the bioavailability of balsalazide is increased by increasing local bioavailability to a surface of the digestive tract.

In another embodiment, the bioavailability of balsalazide is increased compared to administering balsalazide without food.

In one embodiment, the increase in bioavailability of balsalazide is to the colon of a subject.

According to one embodiment, the bioavailability increases due to one or more of a delay of the transit of the balsalazide in the colon of a subject; a decrease in the systemic level of balsalazide in a subject; decrease in the maximal plasma concentration ($C_{max}$) of balsalazide in a subject; delaying $T_{max}$ of balsalazide in a subject; decreasing the extent of absorption ($AUC_{last}$) of balsalazide in a subject; increasing conversion of balsalazide to 5-ASA and 5-ASA to NASA in a subject or increasing the systemic ratio of NASA to 5-ASA in a subject.

In one embodiment, the therapeutically effective amount comprises from between about 6.25 mg to about 14000 mg/day.

In one embodiment, the therapeutically effective amount comprises from between about 750 mg to about 6750 mg/day.

According to one embodiment, the therapeutically effective amount comprises from between about 1100 mg to about 13200 mg/day.

In one embodiment, the therapeutically effective amount is a dosage regimen of three capsules of the formulation three times each day, wherein each capsule comprises about 750 mg of balsalazide.

In another embodiment, the therapeutically effective amount is a dosage regimen of three tablets of the formulation two times each day, wherein each tablet comprises about 1100 mg of balsalazide.

In one embodiment, the therapeutically effective amount is a dosage regimen of one capsule three times each day, wherein each capsule comprises about 750 mg of balsalazide.

In one embodiment, the administration to the subject occurs between about 30 minutes prior to about 1 hour after consuming food.

In one aspect, provided herein are methods the food comprises one or more of applesauce or a high-fat meal.

In one aspect, provided herein are methods of using balsalazide in the treatment of gastrointestinal disorders comprising: administering to a subject in need of treatment a therapeutically effective amount of balsalazide, with food, wherein the administration of the balsalazide with food results in a decrease in at least one of $C_{max}$ and $AUC_{last}$ of balsalazide as compared to administration of balsalazide in a fasted state; and informing the subject that the administration of a therapeutically effective amount of balsalazide in a pharmaceutical composition with food results in one or more of a decrease in at least one of $C_{max}$ and $AUC_{last}$ of balsalazide compared to administration in a fasted state.

In one embodiment, the balsalazide is from a container with printed labeling advising that administration with food results in a decrease in at least one of $C_{max}$ and $AUC_{last}$ of balsalazide compared to administration in a fasted state.

In one embodiment, the printed labeling advises one or more of that the administration of the balsalazide with food results in a decrease in the $C_{max}$ of about 10 to about 70%; the administration of the balsalazide with food results in a decrease in the $AUC_{last}$ of about 10 to about 70%; or the administration of the balsalazide with food results in an increase in a systemic ratio of NASA to 5-ASA of about 10 to about 100%.

Other embodiments of the invention are disclosed infra.

DETAILED DESCRIPTION

Figure 1:
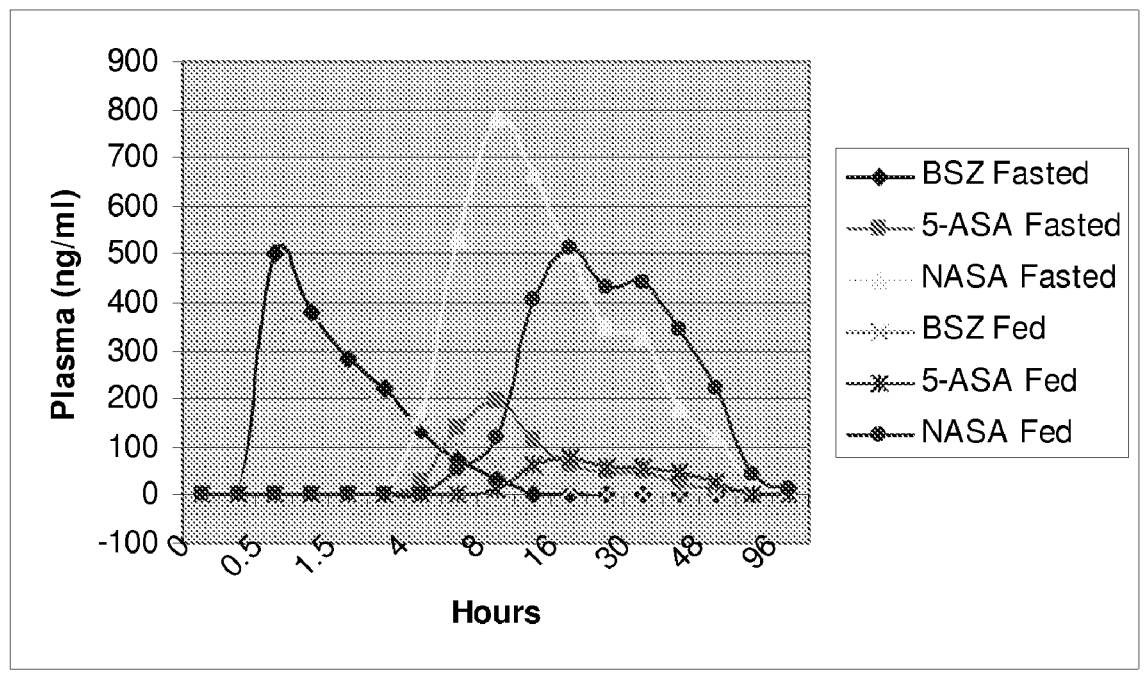
FIG. 1 shows the pharmacokinetic profiles of balsalazide and its key metabolites when administered to human subjects in the fasted and fed state.

Disclosed herein are compositions and methods of treating gastrointestinal disorders by increasing the bioavailability of balsalazides by administering the compositions with food.

Before further description of the present invention, and in order that the invention may be more readily understood, certain terms are first defined and collected here for convenience.

Common pharmacologic term used herein refer are as follows: $T_{max}$ (time to maximum concentration); $C_{max}$ (observed maximum concentration); kel (slope of terminal linear portion of concentration/time curve); $T_{1/2}$ (half-life of balsalazide calculated as: 0.693/Kel); $AUC_{(last)}$ (area under the curve to last quantifiable concentration as measured by the trapezoidal rule); and $AUC_{(inf)}$ (the AUC value extrapolated to infinity calculated as: $AUC_{(inf)}=AUC_{(last)}+C_{(t)last}/Kel$ where $C_{(t)}$last is the last measurable concentration).

The term "administration" or "administering" includes routes of introducing balsalazide to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, eye drops, ointment, suppository, etc. administration by injection, infusion or inhalation; topical by lotion or ointment; and rectal by suppositories. Oral administration is preferred. The injection can be bolus or can be continuous infusion. Depending on the route of administration, balsalazide can be coated with or disposed in a selected material to protect it from natural conditions that may detrimentally effect its ability to perform its intended function. Balsalazide can be administered alone, or in conjunction with either another agent or agents as described above or with a pharmaceutically-acceptable carrier, or both. Balsalazide can be administered prior to the administration of the other agent, simultaneously with the agent, or after the administration of the agent. Furthermore, balsalazide can also be administered in a proform, which is converted into its active metabolite, or more active metabolite in vivo.

"Chemotherapy," as used herein, includes therapies administered systemically for the treatment of neoplastic disease processes (commonly cancer), and may include, for example, biological therapies such as small molecule inhibitors, monoclonal antibodies (e.g., Iressa, Tarceva, Erbitux), or other biological agents administered with a similar objective which may result in symptoms such as those herein described, e.g. those causing a disproportionate incidence of diarrhea or an increased risk of diarrhea.

The term "effective amount" includes an amount effective, at dosages and for periods of time necessary, to achieve the desired result, e.g., sufficient to treat or prevent a bacterial or viral infection. An effective amount of balsalazide may vary according to factors such as the disease state, age, and weight of the subject, and the ability of balsalazide to elicit a desired response in the subject. Dosage regimens may be adjusted to provide the optimum therapeutic response. An effective amount is also one in which any toxic or detrimental effects (e.g., side effects) of balsalazide are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with balsalazide, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition (s), or a suitable assay(s) for the level or activity(ies) of a biomolecule(s), cell(s) or by detection of enteritis or diarrhea within a subject. Amelioration may be transient, prolonged or permanent or it may be variable at relevant times during or after balsalazide is administered to a subject or is used in an assay or other method described herein or a cited reference, e.g., within timeframes described infra, or about 1 hour after the administration or use of balsalazide to about 3, 6, 9 months or more after a subject(s) has received balsalazide.

As used herein, "travel" or "at risk conditions" is intended to include departure and arrival at and being in a destination that may cause diarrhea or behavior that brings a subject into contact with causes of diarrhea or conditions that may cause or exercebate ulcerative colitis or to risk of gastrointestinal cancer, for example, genetic predisposition or to environmental or other causes.

As used herein, "administered with food" refers to, for example, any food product, solid or liquid, with caloric content. Preferably the food is a solid food with sufficient bulk and fat content that it is not rapidly dissolved and absorbed in the stomach. More preferably the food is a meal, such as breakfast, lunch or dinner. The dosage of balsalazide may be administered to the subject, for example, between about 30 minutes prior to about 2 hours after eating a meal, most advantageously the dosage is administered within 15 minutes of eating a meal. The terms "without food", "fasted" and "an empty stomach" refer to, for example, the condition of not having consumed solid food for about 1 hour prior to until about 2 hours after such consumption.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with balsalazide, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after balsalazide is administered to a subject or is used in an assay or other method described herein or a cited reference, e.g., within times descried infra, or about 1 hour of the administration or use of balsalazide to about 3, 6, 9 months or more after a subject(s) has received balsalazide. The term "modulate" may also refer to increases or decreases in the activity of a cell in response to exposure to a balsalazide, e.g., the inhibition of proliferation and/or induction of differentiation of at least a sub-population of cells in an animal such that a desired end result is achieved, e.g., a therapeutic result of balsalazide used for treatment may increase or decrease over the course of a particular treatment.

The term "obtaining" as in "obtaining balsalazide" is intended to include purchasing, synthesizing or otherwise acquiring balsalazide.

The phrases "parenteral administration" and "administered parenterally" as used herein includes, for example, modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The language "a prophylactically effective amount" of a compound refers to an amount of balsalazide which is effective, upon single or multiple dose administration to the subject, in preventing or treating enteritis and/or diarrhea.

The phrases "systemic administration," "administered systemically," "peripheral administration," and "administered peripherally," as used herein mean the administration of balsalazide, drug or other material, such that it enters the subject's system and, thus, is subject to metabolism and other like processes, for example, subcutaneous administration.

The language "therapeutically effective amount" of balsalazide refers to an amount of balsalazide which is effective, upon single or multiple dose administration to the subject, in inhibiting the bacterial growth and/or invasion, or in decreasing symptoms of bacterial infection in a subject with such a bacterial infection sooner that expected in the absence of such treatment. "Therapeutically effective amount" also refers to the amount of a therapy (e.g., a composition comprising balsalazide), which is sufficient to reduce the severity of enteritis and/or diarrhea, reduce the duration of enteritis and/or diarrhea, prevent the advancement of enteritis and/or diarrhea, cause regression of enteritis and/or diarrhea, ameliorate one or more symptoms associated with enteritis and/or diarrhea, or enhance, facilitate, or improve the therapeutic effect(s) of another therapy.

As used herein, the terms "prevent," "preventing," and "prevention" refer to the prevention of the recurrence, onset, or development of enteritis and/or diarrhea or one or more symptoms thereof in a subject resulting from the administration of an abdominopelvic therapy or from travel. Preventing includes protecting against radiation induced enteritis, protecting against radiation induced injury to the mucosa of the colon, protecting against radiation induced colorectal inflammation, and/or radiation-induced inflammation or bacterial invasion of other portions of the alimentary tract. For example, balsalazide may be formulated as a mouthwash to treat or ameliorate radiation-induced esophagitis or other radiation-induced mucositis. For example, balsalazide may be given to a traveler prior to travel to reduce or prevent enteritis or diarrhea.

As used herein, the term "prophylactically effective amount" refers to the amount of a therapy (e.g., a composition comprising balsalazide) which is sufficient to result in the prevention of the development, recurrence, or onset of enteritis and/or diarrhea or one or more symptoms thereof, or to enhance or improve the prophylactic effect(s) of another therapy.

As used herein, the terms "subject" and "subjects" includes organisms which are capable of suffering from a enteritis and/or diarrhea or who could otherwise benefit from the administration of a balsalazide of the invention and refer to an animal, preferably a mammal, including a non-primate (e.g., a cow, pig, horse, cat, or dog), a primate (e.g., a monkey, chimpanzee, or human), and more preferably a human. In a certain embodiment, the subject is a mammal, preferably a human, who has been exposed to or is going to be exposed to an insult that may induce enteritis and/or diarrhea (such as radiation, chemotherapy, or chemical warfare agents or a pathogen encountered during travel). In another embodiment, the subject is a farm animal (e.g., a horse, pig, or cow) or a pet (e.g., a dog or cat) that has been exposed to or is going to be exposed to a similar insult.

Susceptible to gastrointestinal diseases, e.g., enteritis, diarrhea, colon cancer, colitis, is meant to include subjects at risk of developing the gastrointestinal diseases, e.g., subjects receiving or about to receive abdominopelvic therapies, subjects about to travel or subjects that are traveling or otherwise at risk of being exposed to pathogens or conditions, e.g., natural disasters such as floods, hurricanes, earthquakes, tsunamis and the like, subjects who have suffered from colitis in the past, subjects having a family history of colitis or cancer and the like.

As used herein the terms "radiation," "radiation therapy," "radiotherapy," and "irradiation" refer to any exposure to ionizing radiation whether intentional or unintentional, malicious or therapeutic, and may include, for example, external beam radiotherapy, photon radiotherapy, electron radiotherapy, proton radiotherapy, carbon ion radiotherapy, lithium ion radiotherapy, silicon ion radiotherapy, helium ion radiotherapy, other forms of hadrontherapy or other particle therapy, brachytherapy, radioisotope therapy, injectable isotopes, e.g., isotopes adhered to or within or admixed with a matrix of any sort, or any radiation exposure that is unintentional or malicious, independent of the agent or agents employed.

As used herein, the terms "treat," "treatment," and "treating" refer to the reduction of the progression, severity, and/or duration of enteritis and/or diarrhea or amelioration of one or more symptoms thereof, wherein such reduction and/or amelioration result from the administration of one or more therapies (e.g., a composition comprising balsalazide).

"Abdominopelvic therapies" include, for example, radiation therapy, chemotherapy, surgery, or a combination thereof. The therapies may be administered simultaneously or one after the other in any timeframe determined, for example, by a healthcare professional.

Radiation may be a result of, e.g., radiation therapy, accidental radiation exposure, and radiation exposure from a terrorist attack. See e.g., Moulder, Int. J. Radiat. Biol. 80:3-10 (2004). Chemical insults are commonly from chemotherapy. Enteritis (mucositis of intestines, especially the small intestine) is common in subjects who receive abdominal or pelvic radiation therapy, cytotoxic agents, or a combination thereof. The main symptoms are nausea, abdominal pain, bloating, and diarrhea. Radiation-induced diarrhea often occurs during the first two weeks after beginning of radiation therapy. Without wishing to be bound by any particular scientific theory, the mechanism of radiation-induced diarrhea involves acute mechanical damage to the epithelial crypt cells of the gastrointestinal tract. Such damage results in cell death (via either a necrotic or apoptotic mechanism), inflammation, and ulceration of the intestinal mucosa, which is then exposed to irritating bile salts and becomes susceptible to opportunistic infections. See e.g., Gwede, Seminars in Oncology Nursing 19:6-10 (2003). Chemotherapeutic agents that commonly associated with diarrhea include, but are not limited to, fluoropyrimidines (e.g., 5-fluorouracil and the more recently developed prodrug capecitabine), topisomerase I inhibitors (e.g., irinotecan, topotecan), and other agents (e.g., cisplatin, oxaliplatin, cytarabine). See e.g., Viele, Seminars in Oncology Nursing 19:2-5 (2003). Chronic bowel toxicity may also occur after radiation therapy, usually six months to three years after the therapy. Subjects often have intermittent constipation and diarrhea, which may cause malnutrition and disturbance of electrolytes. In severe cases, acute intestinal obstruction, fistulas, or bowel perforation may occur. See e.g., Keefe et al., Seminars in Oncology 20:38-47 (2004). Radiation therapy and radiotherapy are used interchangeably herein and include external irradiation and internal irradiation, also referred to as brachytherapy, intracavitary brachytherapy, or interstitial brachytherapy. Radiation sources contemplated include pure Gamma emitters, pure Beta emitters, alpha emitters, neutron emitters, other ion emitters, and mixed irradiations.

Determining a subject in need thereof may be by one or more of hydrogen breath testing, symptom analysis, or medical assessment and other methods described infra.

As used herein, the terms "chemotherapy" and "chemotherapeutic agents" are used interchangeably and refer to chemotherapeutic agents or drugs exhibiting anti-cancer effects and used in the treatment of malignancies.

We have surprisingly found that the administration of balsalazide to a subject experiencing radiation induced enteritis, reduces symptoms of the condition and that administering with food increases the bioavailability of balsalazide to the digestive tract. This permits greater targeting of the symptoms' cause and results in improved efficacy of symptom amelioration, while at the same time causing fewer adverse effects, as would be commonly seen with supportive measures such as traditional anti-diarrheals. The use of balsalazide to treat radiation induced enteritis is especially beneficial because when administered enterally, it is not associated with substantial absorption of drug, and thus decreases the probability of drug-drug interactions, which are common in subjects on chemotherapy and/or radiotherapy, or subjects with cancer. This is seen in terms of greater targeting of therapy, fewer drug interactions, and improved tolerance to therapy. Particular benefit is seen with this therapy because it may prevent or ameliorate symptoms that would otherwise necessitate a break in treatment to allow the subject to recover from their symptoms. Treatment breaks are associated with decreased treatment efficacy, thus indirectly, this invention is likely to improve cure rates for cancer and other neoplastic disease through a mechanism of improved tolerance to treatment.

As used herein radiation induced enteritis includes, for example, radiation induced injury to the abdominopelvic area from irradiation of the abdominopelvic region. Irradiation often causes acute radiation esophagitis, gastritis, enteritis or colorectal toxicity. Symptoms may include dysphagia, odynophagia, diarrhea, dyspepsia, proctitis, stool incontinence, cramping abdominal pain, bloating, nausea, loose stool, increased defecations per day, tenesmus, mucous production, abdominopelvic pain, and peri-rectal discomfort. Acute radiation enteritis and/or proctosigmoiditis results largely from irritation of the small bowel, sigmoid colon and rectum.

As used herein, the terms "chemotherapy" and "chemotherapeutic agents" are used interchangeably and refer to chemotherapeutic agents or drugs exhibiting anti-cancer effects and used in the treatment of malignancies.

It has surprisingly been found that the administration of balsalazide to a subject experiencing radiation induced enteritis, reduces symptoms of the condition. The success of, for example, balsalazide in the treatment of radiation enteritis is surprising because of the failure of other related 5-ASA drugs, such as osalazine and mesalamine, in clinical trials.

Balsalazide is the generic name for a 2-hydroxy-5-phenylazobenzoic acid derivative in which an aminosalicylate moiety, 5-aminosalicylic acid (5-ASA) (mesalamine), is linked to a carrier molecule, 4-aminobenzoyl-$\beta$-alanine (4-ABA), through an azo-bond. Disodium balsalazide is highly water-soluble and is cleaved in the colon to release mesalamine, which is the therapeutically active portion of the molecule, as well as 4-aminobenzol-$\beta$-alanine, which is the carrier moiety. Mesalamine is 5-aminosaliacylic acid and appears to act topically.

The use of balsalazide to treat gastrointestinal disorders is especially beneficial because balsalazide is metabolized by intestinal microflora to the active form, 5-ASA, thus ensuring optimal delivery of the active drug to the bowel without loss via absorption more proximally in the intestinal tract. Balsalazide also exhibits fewer side effects than other 5-ASA prodrugs and it may be administered to subjects with sulpha allergies. Balsalazide is also beneficial because the active component has been demonstrated to directly scavenge free radicals, which may reduce subsequent inflammatory response. Without wishing to be bound by any particular theory, we believe that balsalazide may protect against radiation-induced enteritis by blocking the mediators of inflammation and the release of free radicals in the rectal mucosa.

As used herein, "radiation induced enteritis," includes radiation induced injury to the pelvic area from irradiation of the pelvic region. Irradiation often causes acute radiation enteritis or colorectal toxicity. Symptoms may include diarrhea, proctitis, stool incontinence, loose stool, increased defecations per day, tenesmus, mucous production, abdominopelvic pain, and peri-rectal discomfort. Acute radiation enteritis results largely from irritation of the sigmoid colon and rectum.

Dosages, according to certain preferred embodiments, range from between about 6.25 mg to about 14000 mg of balsalazide administered daily. For example, a dose of 1100 mg may be administered to a subject twice daily. Other appropriate dosages for methods according to this invention may be determined by health care professionals or by the subject. The amount of balsalazide administered daily may be increased or decreased based on the weight, age, health, sex or medical condition of the subject. One of skill in the art would be able to determine the proper dose for a subject based on this disclosure.

Methods of Treatment

Described herein are methods of treating subjects suffering from or susceptible to gastrointestinal disorders by administering one or more balsalazides to a subject with food. The administration of balsalazide with food increases the bioavailability and efficacy of the compound. The administration of food, as will be described below also increases the bioavailability of 5-ASA to the colon of a subject, as well as delaying the transit of 5-ASA in the colon of a subject, decreasing systemic level of 5-ASA in a subject leading to fewer side effects and greater subject compliance to treatment.

According to one aspect, provided herein are methods of increasing the bioavailability of balsalazide, comprising administering to the subject a therapeutically effective amount of balsalazide with food, wherein the bioavailability of balsalazide is increased compared to administering balsalazide without food. Without wishing to be bound by any particular theory, the bioavailability of balsalazide is due to delay in transit of the metabolite 5-ASA and an increase in the exposure of the gastrointestinal tract with 5-ASA. This also has the advantage of decreasing the amount systemically adsorbed 5-ASA, thus reducing the side effects and increasing patient compliance.

According to one aspect, provided herein are methods of increasing the bioavailability of 5-ASA to the colon of a subject comprising administering to a subject in need thereof a therapeutically effective amount of balsalazide with food, wherein the bioavailability of 5-ASA is increased compared to administering balsalazide without food.

According to one aspect, provided herein are methods of delaying the transit of 5-ASA in the colon of a subject comprising, administering a therapeutically effective amount of balsalazide to a subject in need thereof with food, wherein the transit of 5-ASA is increased compared to administering balsalazide without food. Without wishing to be bound by any particular theory, the delay in transit of the 5-ASA due to administration of balsalazide with food increases the exposure of the gastrointestinal tract with 5-ASA and decreases the amount systemically adsorbed, thus reducing the side effects and increasing patient compliance.

According to one aspect, provided herein are methods for decreasing systemic level of 5-ASA in a subject comprising, administering to a subject in need thereof a therapeutically effective amount of balsalazide with food, wherein the systemic level of 5-ASA is decreased compared to administering balsalazide without food. The decrease in systemic levels of 5-ASA upon administration of balsalazide with food reduces side effects and increases subject compliance.

According to one aspect, provided herein are methods of decreasing the maximal plasma concentration ($C_{max}$) of balsalazide in a subject comprising, administering to a subject in need thereof a therapeutically effective amount of balsalazide with food, wherein the $C_{max}$ of balsalazide is increased compared to administering the 5-aminosalicylate without food.

According to one aspect, provided herein are methods of delaying $T_{max}$ of balsalazide in a subject comprising, administering to a subject in need thereof a therapeutically effective amount of balsalazide with food, wherein the $T_{max}$ of balsalazide is delayed compared to administering balsalazide without food.

According to one aspect, provided herein are methods of decreasing the extent of absorption ($AUC_{last}$) of balsalazide in a subject comprising, administering to a subject in need thereof a therapeutically effective amount of balsalazide with food, wherein the $AUC_{last}$ of balsalazide is decreased compared to administering balsalazide without food.

According to one aspect, provided herein are methods of increasing the systemic ratio of NASA to 5-ASA in a subject comprising, administering to a subject in need thereof a therapeutically effective amount of balsalazide with food, wherein the systemic ratio of NASA to 5-ASA is increased compared to administering balsalazide without food.

According to one aspect, provided herein are methods of increasing the conversion of 5-ASA to NASA in a subject comprising, administering to a subject in need thereof a therapeutically effective amount of balsalazide with food, wherein the conversion of 5-ASA to NASA is increased in a subject administered a therapeutically effective amount of balsalazide compared to administering a 5-aminosalicylate without food.

According to the methods described herein, balsalazide comprises, for example, one or more of mesalamine, sulphasalazine, olsalazine, ipsalazine, salicylazobenzoic acid, or balsalazide.

Therapeutically effective amounts, according to the methods described herein include doses from between about 6.25 mg to about 14000 mg/day, for example, as tablets or capsules. The therapeutically effective amount also comprises from between about 750 mg to about 6750 mg/day, for example, as tablets or capsules. The therapeutically effective amount may also comprises from between about 1100 mg to about 13200 mg/day, for example, as tablets or capsules. Therapeutically effective amounts and dosage regimens include, administering three tablets or capsules of the formulation three times each day, wherein each tablet or capsule comprises about 750 mg of balsalazide. Therapeutically effective dosage regimes also include, for example, two tablets of the formulation three times each day, wherein each tablet or capsule comprises about 1125 mg of balsalazide. Therapeutically effective amounts and dosage regimens further include, for example, one tablet or capsule three times each day, wherein each tablet or capsule comprises about 2250 mg of balsalazide. Other dosage regime examples useful according to the methods described herein include, for example, a dosage regime ranging from between about 1 to about 14 g per 70 kg body weight per day.

The administration to the subject occurs, for example, between about 30 minutes prior to about 2 hours after consuming food. The administration with food may also be at the same time as the consumption of the food. Also, the administration to the subject may be, for example, immediately after the consumption of food up to about 1 hour after the consumption. The food may comprise, for example, applesauce or a high-fat meal.

Balsalazide may be administered by one or more of a non-systemic delivery route or a systemic delivery route. Non-systemic delivery routes, include, for example, one or more of a colonic delivery route, an ingestive delivery route, a topical application of a cream, gel, and/or ointments. Systemic delivery routes, include, for example, ingestion, injection, intravenous drip, implant, a transdermal delivery route, and/or a transmucosal delivery routes.

According to one aspect, provided herein are methods of decreasing the rate and extent of absorption of an oral dosage form of balsalazide as measured by the drug concentration or metabolite thereof attained in the blood stream over time in a subject comprising, administering to the subject a therapeutically effective amount of balsalazide in a pharmaceutical composition with food. For example, the systemic levels of 5-ASA are decreased while the systemic levels of NASA may increase.

In one embodiment, the balsalazide is from a container comprising labeling advising that administration with food results in a decrease in the maximal plasma concentration ($C_{max}$) and extent of absorption ($AUC_{last}$) of balsalazide compared to administration without food.

According to one aspect, provided herein are methods of using balsalazide in the treatment of gastrointestinal disease comprising: informing a subject with a gastrointestinal disease that the administration of a therapeutically effective amount of balsalazide with food results in a decrease in at least one of $C_{max}$, $AUC_{last}$, or systemic adsorption of 5-ASA compared to administration without food.

According to one aspect, provided herein are methods of using balsalazide in the treatment of gastrointestinal disorders comprising altering the oral bioavailability of balsalazide by: obtaining balsalazide from a container providing information that administration of balsalazide with food increases the bioavailability of balsalazide or a metabolite thereof to the colon of the subject compared to administration without food, and ingesting the balsalazide with food.

According to one aspect, provided herein are methods of using balsalazide in the treatment of gastrointestinal disorders comprising: administering to a subject in need of treatment a therapeutically effective amount of balsalazide, with food, wherein the administration of the balsalazide with food results in a decrease in at least one of $C_{max}$ and $AUC_{last}$ of balsalazide as compared to administration of balsalazide in a fasted state; and informing the subject that the administration of a therapeutically effective amount of balsalazide in a pharmaceutical composition with food results in one or more of a decrease in at least one of $C_{max}$ and $AUC_{last}$ of balsalazide compared to administration in a fasted state.

The balsalazide is from, for example, a container with printed labeling advising that administration with food results in a decrease in at least one of $C_{max}$ and $AUC_{last}$ of balsalazide compared to administration in a fasted state. The balsalazide may be provided, for example, as a table, a capsule, a loose powder, a sachet, and the like. For example, balsalazide is provided in 750 mg capsule form.

The printed labeling may advise, for example, that the administration of the balsalazide with food results in a decrease in the $C_{max}$ of about 10 to about 70%, or from about 20 to about 50%. The printed labeling may also advise, for example, that the administration of the balsalazide with food results in a decrease in the $AUC_{last}$ of about 10 to about 70%. The labeling may further advise, for example, that the administration of the balsalazide with food results in an increase in systemic ratio of NASA to 5-ASA of about 10 to about 100%, or from about 20 to about 80%. For example, the ratio of NASA to 5-ASA may be increased 6-fold to about 8-fold compared to administration without food.

According to one aspect, provided herein are methods of inhibiting the growth of a bacterial species in a human subject, comprising administering to a human subject having a bacterial infection or overgrowth a pharmaceutically acceptable composition containing balsalazide in a dose effective to inhibit the growth of a bacterial species in the human subject with food. Bacterial species in which the infection may be reduced or eradicated include, for example, one or more of a *Clostridium* species, or other anaerobic or aerobic bacterial species. *Clostridium* species, include, for example, *Clostridium perfringens, Clostridium difficile, Clostridium botulinum*, and/or *Clostridium tetani*.

According to one aspect, a method of treating a subject suffering from a gastrointestinal disease comprises administering to the subject a therapeutically effective amount of a formulation comprising: administering balsalazide with food. In one embodiment, balsalazide is sodium balsalazide dihydrate. In one embodiment, the pharmaceutical composition is administered orally to an individual suffering from or at risk to develop a gastrointestinal disorder in a daily dosage ranging from 1 to 14 g per 70 kg body weight per day.

In another embodiment, the gastrointestinal disease is active ulcerative colitis. In yet another embodiment, the gastrointestinal disease is colon cancer.

In another embodiment, the bacterial species is an obligate anaerobe.

In a related embodiment, the bacterial species is a *Clostridium* species. In another related embodiment, the bacterial species is *Clostridium perfringens, Clostridium difficile, Clostridium tetani* or *Clostridium botulinum*. In one embodiment, balsalazide is formulated in a delivery system to deliver a dose between 6.25 and 150 mg/day. In another embodiment, the dose comprises between about 12.5 and about 200 mg/day. In another embodiment, balsalazide formulated in a delivery system to deliver a dose over 6,450 mg/day.

In certain embodiment, the pharmaceutical compositions of balsalazides are formulated, for example, for human, pediatric, or veterinary use (e.g., domestic or farm animal, non-human mammal, bird, non-human primate, mouse, rat, rabbit, gerbil, hamster, canine, feline, ovine, bovine, swine, pachyderm, equine, marine mammal, a duck, chicken, goose, turkey, ostrich, emu, dove, pigeon, quail, pheasant, peafowl, or guinea fowl).

Yet another aspect of this invention is providing information to prescribing physicians and subjects receiving balsalazide therapy useful in maximizing the therapeutic effect of the oral dosage form, by recommending that balsalazide be taken within about half an hour of consuming food.

The effect of food on balsalazide absorption was identified in a study designed to compare the bioavailability of balsalazide in the formulation the drug product, which was administered to healthy volunteers with and without food.

Yet another aspect of this invention relates to a method of treating a subject with balsalazide who is in need thereof. Identifying a subject in need of such treatment can be in the judgment of a subject or a health care professional and can be subjective (e.g., opinion) or objective (e.g., measurable by a test or diagnostic method).

Balsalazide may be administered prior to, during, and/or after the treatment therapies or travel or exposure to other at risk conditions. Balsalazide may be administered, for example, once a day, twice a day, three times a day, or four times a day. Balsalazide may be administered in doses, for example of from about between 6.25 mg to about 14000 mg/day. Another example is administering balsalazide from between about 750 mg to about 6750 mg/day. Balsalazide may be administered, for example, in tablet form, powered form, liquid for or in capsules.

Subjects in need thereof include subjects that will undergo radiation therapy, either alone or in combination with other pelvic therapies that could induce enteritis or inflammation of portions of the alimentary tract. This need may be apparent prior to undergoing radiation therapy, chemotherapy, a pelvic surgical procedure or a combination of therapies; while a subject is undergoing radiation therapy, chemotherapy, a pelvic surgical procedure or a combination of therapies; and after a subject has under gone radiation therapy, chemotherapy, a pelvic surgical procedure, or a combination of therapies. For example, a subject may be about to undergo, may be undergoing, or have undergone radiation therapy in combination with chemotherapy or a surgical procedure.

Also included are subjects who are or who may be susceptible to enteritis. Subjects may be suffering from, for example, gastrointestinal malignancies, including colorectal, appendiceal, anal, pancreatic, hepatobiliary, esophageal, gastric, gastroesophageal junction or small bowel cancers; urogenital malignancies, including prostate, bladder, testicular, or penile cancers; gynecologic malignancies, including cervical, endometrial, ovarian, vaginal, or vulvar cancers; or osteogenic and other sarcomatous malignancies in which abdominopelvic structures are involved, or the subject may be or may be about to travel to a location where they may be susceptible to coming into contact with a pathogen or other conditions that may lead to traveler's diarrhea.

As used herein, a therapeutically effective amount means an amount effective, when administered to a human or non-human subject, to provide a therapeutic benefit such as an amelioration of symptoms, e.g., an amount effective to decrease the symptoms of acute radiation enteritis.

According to certain embodiments, balsalazide may be administered prior to radiotherapy. Balsalazide may be administered, for example, at least one day prior to the subject's first dose of radiotherapy, at least five days prior to the subject's first dose of radiotherapy, during radiation therapy, for at least one day after the cessation of radiation therapy, for fourteen days after the cessation of radiation therapy, or a combination of before, during and after. These time frames are for general reference and the duration of treatment may be determined by a health care professional on a subject by subject basis. Administration at least five days prior to the therapy includes administration daily, every day prior to the pelvic therapy, administration on a majority of days prior the therapy, administration on the day of treatment or no administration on the day of treatment.

Certain preferred embodiments include administering balsalazide from at least one day prior to the first dose of radiotherapy until at least one day after the cessation of radiation therapy. Treatment prior to the radiation therapy allows for balsalazide to be present at its site of action during the cause of the injury.

In certain embodiments, balsalazide is administered to a subject from between about 2 weeks to about 6 weeks in duration, from between about 8 weeks to about 12 weeks in duration, or from between 1 day to about 7 days. Balsalazide may be administered intermittently or continuously during the course of treatment. Length of treatment may vary depending of the type and length of radiotherapy, chemotherapy, and/or type of surgical procedure and the proper length of treatment may be easily determined by one of skill in the art having the benefit of this disclosure.

For any of the embodiments, balsalazide may be administered, for example, once daily, twice daily, three times daily, or four times daily to a subject. In some particularly preferred methods of the present invention comprise administering balsalazide twice daily to the subject because it may, for example, minimize the side effects and increase subject compliance.

Dosages, according to certain preferred embodiments, range from between about 6.25 mg to about 1400 mg of balsalazide administered daily. Other appropriate dosages for methods according to this invention may be determined by health care professionals or by the subject. The amount of balsalazide administered daily may be increased or decreased based on the weight, age, health, sex or medical condition of the subject. One of skill in the art would be able to determine the proper dose for a subject based on this disclosure.

For subjects undergoing multiple therapies, balsalazide may be administered, for example, at least one day prior to the subject's first dose of radiotherapy, chemotherapy, and/or prior to undergoing a surgical procedure; at least five days prior to the subject's first dose of radiotherapy, chemotherapy, and/or prior to undergoing a surgical procedure; during radiation therapy, chemotherapy, and/or the surgical procedure; at least one day after the cessation of radiation therapy, chemotherapy, or after the surgical procedure; for fourteen days after the cessation of radiation therapy, chemotherapy, or after the surgical procedure.

It is often preferable to administer balsalazide to a subject prior to treatment, during treatment, as well as after the cessation of treatment. For example, balsalazide may be administered from at least one day prior to the first dose of radiotherapy, chemotherapy, and/or prior to undergoing the surgical procedure until at least one day after the cessation of radiation therapy, chemotherapy, or the surgical procedure.

Indications include a subject receiving radiotherapy, chemotherapy, and/or surgical procedure as a result of treatment for cancer of the cervix, prostate, appendix, colon, intestine, rectum, pancreas, liver, small bowel, esophagus, stomach, gastroesophageal junction, or other gastrointestinal malignancy, or prostatectomy.

According to certain embodiments, balsalazide may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents. For example, cisplatin, carboplatin, docetaxel, paclitaxel, fluorouracil, capecitabine, gemcitabine, irinotecan, topotecan, etoposide, mitomycin, gefitinib, erlotinib, cetuximab, bevacizumab, iressa, tarava, erbitux, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, rifaximin, diphenoxylate with atropine, and/or loperamide.

The methods disclosed herein are also useful for protecting a subject against radiation induced enteritis or other alimentary tract inflammation by administering to a subject in need thereof a therapeutically effective amount of balsalazide. For example, prophylactic doses may be administered prior to a subject undergoing radiation.

The methods disclosed herein are useful for protecting a subject against radiation induced injury to the mucosa of the colon, as well as against radiation induced colorectal inflammation or other alimentary mucositis by administering to a subject in need thereof a therapeutically effective amount of balsalazide.

In yet another aspect, a method of treating a subject suffering from or susceptible to enteritis and/or diarrhea comprising administering to a subject in need thereof a therapeutically effective amount of a balsalazide formulation, to thereby treat the subject. Upon identification of a subject suffering from or susceptible to enteritis and/or diarrhea, for example, radiation induced enteritis or traveler's diarrhea, balsalazide is administered.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, the gastro-resistant balsalazide formulation is administered twice per day. In other embodiments, the gastro-resistant balsalazide formulation is administered for from between about 1 day to about 7 days, or for example, for about 7 days/month for from between about 1 month to about 36 months, or once or twice daily for from between about 1 month to about 36 months or more.

In certain embodiments, one or more formulations of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, e.g., the cycle in order to reduce the development of resistance to one of the therapies, to avoid or reduce the side effects of one of the therapies, and/or to improve the efficacy of the therapies.

In certain embodiments, the administration of the same formulations of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a gastro-resistant balsalazide formulation may be repeated and the administration may be separated by at least at least 1 day, 2 days, 3 days, 5 days, 10 days, 15 days, 30 days, 45 days, 2 months, 75 days, 3 months, or at least 6 months.

Certain indications may require longer treatment times. Short-term treatments include, for example, treatment for 1 to about 7 days. Long-term treatments with balsalazide, include for example, treatment for 15 days, 3 months, 9 months, 7 days/month for three months, 7 days/month for three to twelve months or any time in-between or longer. One of skill in the art, having the benefit of this disclosure would understand how to vary the dosage for a particular subject or intended result. Dosage regimens will vary depending on the age, size, and condition of the subject. For example, depending on the severity of the disease, or injury whether it is a new disease state or a relapse or recurrence, etc.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays, animal studies, and human studies can be used in formulating a range of dosage of the prophylactic and/or therapeutic agents for use in humans. The dosage of such agents is preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (e.g., the concentration of the test compound that achieves a half-maximal inhibition of symptoms) as determined in cell culture. Such information can be used to more accurately determine useful doses in humans. Levels in plasma may be measured, for example, by high performance liquid chromatography.

The amount of the composition of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each subject's circumstances.

The total daily dosage of balsalazide formulations, for example of balsalazide, can range from about 6.25 mg to about 14000. For example, in general, the total daily adult dosage of balsalazide in formulations of the present invention ranges from about 750 mg to about 6750 mg, about 1100 to about 13200 mg, about 6000 to about 7000 mg, or any whole number or fractional amount in between. A single dose may be formulated to contain about 250, 275, 400, 600, 525, 550, 575, 750, 800 or 1000 mg of balsalazide. In one embodiment, a single dose contains about 750 mg of balsalazide.

Balsalazide may be provided as modified-release formulations or as membrane-controlled formulations. Membrane-controlled formulations of the present invention can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and the functional coating, a barrier or sealant may be applied. The barrier or sealant may alternatively, or additionally, be provided between the rapid release core and the membrane coating.

Balsalazide formulations may be of any polymorphic or amorphous form of balsalazide.

In an embodiment, balsalazide is administered to the subject using a pharmaceutically-acceptable formulation, e.g., a pharmaceutically-acceptable formulation that provides sustained delivery of balsalazide to a subject for at least 12 hours, 24 hours, 36 hours, 48 hours, one week, two weeks, three weeks, or four weeks after the pharmaceutically-acceptable formulation is administered to the subject.

In some embodiments, it may be desirable to administer the pharmaceutical compositions of the invention locally to the area in need of treatment. This may be achieved by, for example, local infusion during surgery, or topical application, e.g., in conjunction with a wound dressing after surgery, by injection, by means of a catheter, by means of a suppository, or by means of an implant (the implant being of a porous, non-porous, or gelatinous material, including membranes, such as sialastic membranes, or fibers). In one embodiment, administration can be by direct injection at the site (or former site) of rapidly proliferating tissues that are most sensitive to an insult, such as radiation, chemotherapy, or chemical/biological warfare agent. In another embodiment, balsalazide can be formulated in a viscous or non-viscous solution for oral administration. In a separate embodiment, balsalazide can be formulated in a viscous or non-viscous mixture containing a pain reliever, e.g., lidocaine, to ameliorate radiation-induced oral mucositis or esophagitis. In a separate embodiment, balsalazide can be formulated in a viscous or non-viscous mixture containing, for example, sucralfate to ameliorate radiation-induced oral mucositis or esophagitis. In a separate embodiment, balsalazide can be formulated in a viscous or non-viscous mixture containing, for example, nystatin to ameliorate radiation-induced oral mucositis or esophagitis. In a separate embodiment, balsalazide can be formulated in a viscous or non-viscous mixture containing a combination of the above and the like to ameliorate radiation-induced oral mucositis or esophagitis.

In certain embodiments, these pharmaceutical compositions of balsalazide are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Balsalazide and Pharmaceutical Compositions

Balsalazide is the generic name for Colazal®. Examples of uses and manufacture of balsalazides may be found, for example in U.S. Pat. Nos. 6,197,341; 5,905,073; 5,498,608; and 6,326,364; which are hereby incorporated by reference in their entirety. Balsalazide is useful in the methods described herein to increase their bioavailability and efficacy.

The drug product, COLAZAL, contains 750 mg of balsalazide disodium in a hard gelatin capsule for oral delivery. When taken orally, 99% of the prodrug balsalazide reaches the colon, where the presence of colonic bacterial azo-reductase enzyme reduces the diazo bond, thereby liberating the 5-ASA for topical activity in the colon (Colazal® (balsalazide disodium) Capsules 750 mg Package Insert 0004.1/July 2000). The released 4-ABA carrier component is poorly absorbed and largely eliminated in the feces (Ragunath K and Williams J G. Aliment Pharmcol. Ther. 2001; 15:1549-1554). The local presence of 5-ASA is the basis for the effectiveness of this class of drugs and mucosal 5-ASA concentrations are correlated inversely with UC disease activity (Frieri G, Giacomelli R, Pimpo M. et al. Gut 2000; 47:410-414). While the actual mechanism of action of 5-ASA is not completely understood, systemic exposure of 5-ASA is thought to be responsible for the sides effects associated with treatment. Most prevalent in studies on balsalazide is headache (Green J B Gastroenterology 1999; 117:1513-1514) and lower systemic levels of 5-ASA may contribute to a lower incidence of headache as observed in some trials (Levine D S, Riff D S, Pruitt R et al. Am. J. Gastroenterol. 2002; 9:1398-1407). Dose regimens that increase the local mucosal concentration of the active therapeutic moiety and decrease the systemic absorption of 5-ASA are therefore preferred.

While 5-ASA is the active therapeutic moiety of balsalazide, it is rapidly converted to the metabolite N-acetyl-5-ASA (NASA) in the mucosa (Allgayer H, Ahnfelt N O, Kruis W et al Gastroenterology. 1989; 97:38-41). Approximately, 12% of the oral dose can be measured in the blood as this metabolite as compared to <2% of the oral dose of 5-ASA that is systemically absorbed (van Hogezand R A, van Hees P A, van Gorp J P, van Lier H J, Bakker J H, Double-blind comparison of 5-aminosalicylic acid and acetyl-5-aminosalicylic acid suppositories in subjects with idiopathic proctitis. Aliment Pharmacol Ther. 1988 February; 2(1):33-40). NASA is known to be of lower anti-inflammatory activity in the colon (Colazal® (balsalazide disodium) Capsules 750 mg Package Insert September 2006)), and is therefore thought to be less toxic when in the systemic circulation. Thus, dose regimens that decrease the systemic level of total mesalamine (5-ASA and NASA) and increase the systemic level of NASA at the expense of decreasing the level of 5-ASA (i.e. the ratio of NASA to 5-ASA) in the systemic circulation are preferred. Dose regimens that delay the transit of 5-ASA in the colon will also result in an increase in contact time with the colonic mucosa, and could therefore increase efficacy of the drug. This increased contact time with the colonic mucosa will also result in an increased systemic ratio of NASA to 5-ASA. A previous study comparing balsalazide to a pH-dependent release formulation of mesalamine showed that greater efficacy, as measured by sigmoidoscopic scoring of the inflamed mucosa, was associated with a lower systemic level of 5-ASA and a higher ratio of systemic NASA to 5-ASA (Levine D S, Riff D S, Pruitt R et al. Am. J. Gastroenterol. 2002; 9:1398-1407). The present disclosure shows that dosing human subjects with balsalazide in the fed state is a dose regimen that achieves these goals.

Article of Manufacture

The article of manufacture comprises, for example, a container holding an immediate release pharmaceutical composition suitable for oral administration of balsalazide in combination with printed labeling instructions providing a discussion of when a particular dosage form should be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect of this invention is an article of manufacture that comprises a container containing a pharmaceutical composition comprising balsalazide wherein the container holds preferably balsalazide composition in unit dosage form and is associated with printed labeling instructions advising of the differing absorption when the pharmaceutical composition is taken with and without food.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing balsalazide include, for example, those suitable for oral, nasal, topical (including buccal and sublingual), rectal, vaginal, aerosol percutaneous, and/or parenteral administration. For instance, to treat an infected external biliary drain, balsalazide could be administered percutaneously via that drain, thus resulting in an "intrabiliary" administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, more preferably from about 10% to about 30% active ingredient.

Methods of preparing these balsalazide compositions include the step of bringing into association balsalazide with the carrier and, optionally, one or more accessory ingredients. In general, the formulations are prepared by uniformly and intimately bringing into association with balsalazide with liquid carriers, or finely divided solid carriers, or both, and then, if necessary, shaping the product.

Balsalazide compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of balsalazide as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of balsalazide include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active balsalazide may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing balsalazide with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of balsalazide include powders, sprays, ointments, pastes, creams, lotions, gels, solutions, patches and inhalants. Balsalazide may be mixed under sterile conditions with a pharmaceutically-acceptable carrier, and with any preservatives, buffers, or propellants which may be required.

The ointments, pastes, creams and gels may contain, in addition to balsalazide of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to balsalazide, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Balsalazide can be alternatively administered by aerosol. This is accomplished, for example, by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the invention suitable for parenteral administration comprise one or more balsalazide in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution that in turn may depend upon crystal size and crystalline form. Alternatively, delayed absorption of a parenterally-administered drug form is accomplished by dissolving or suspending the drug in an oil vehicle.

Injectable depot forms are made by forming microencapsule matrices of balsalazide in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When balsalazide are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

In some cases, to ameliorate, for example, simultaneously, conditions associated with the condition for which balsalazide is administered, such as pain, candida, dysphagia, odynophagia, mucositis, esophagitis, pneumonitis, stomatitis, or xerostomia, balsalazide may be formulated as a combination with other appropriate agents including but not limited to nystatin, ketoconazole, fluconazole, lidocaine, benzocaine, diphenhydramine, dimenhydrinate, azelastine, cetirizine, hydrocortisone, prednisone, prednisolone, dexamethasone, triamcinolone, beclomethosone, budesonide, mometasone, or other steroid, local anesthetic, anti-fungal, or antihistamine agents. This formulation may take the form of a viscous or non-viscous liquid, a topically applied compound, an aerosol, or an injectable.

Regardless of the route of administration selected, balsalazide, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular subject, composition, and mode of administration, without being toxic to the subject. Exemplary dosage forms are disclosed infra.

Packaged compositions are also provided, and may comprise a therapeutically effective amount of balsalazide. Balsalazide and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

It should be appreciated that the invention should not be construed to be limited to the example, which is now described; rather, the invention should be construed to include any and all applications provided herein and all equivalent variations within the skill of the ordinary artisan.

The systemic levels of balsalazide, 5-ASA and NASA were measured after a single 2.25 g (3×750 mg) oral dose of balsalazide disodium administered (1) as an intact capsule following an overnight fast, or (2) as an intact capsule following a high-fat breakfast. Healthy male subjects between 18 and 45 years of age, who were nonsmokers for at least 2 years prior to the study, and had a negative urine test for selected drugs of abuse and a negative alcohol (ETOH) were used. Study periods were separated by a minimum of 4 days. Standard pharmacokinetic parameters were computed from the plasma ($C_{max}$, $T_{max}$ and $AUC_{last}$) and urine (% excreted and Clr) concentrations for balsalazide and its metabolites (5-ASA, N-Ac-5-ASA, 4-ABA and N-Ac-4-ABA) for the 17 subjects who completed the two study periods as per protocol. The full pharmacokinetic profiles observed for dosing under these two conditions are shown in FIG. 1. The delay in appearance of and the lower levels of 5-ASA and NASA can clearly be observed. The standard pharmacokinetic parameters are shown for both dosing conditions in Table 1.

TABLE 1

Summary of Pharmacokinetic Parameters for Capsule Formulated Balsalazide in Study BZPK1001

| | Treatment A Fasting n = 17 | Treatment B High-fat Diet n = 17 | A vs. B p value [a] |
|---|---|---|---|
| $C_{max}$ (ng/mL) | | | |
| Balsalazide | 511.5 ± 323.18 | 446.3 ± 389.90 | 0.187 |
| 5-ASA | 218.3 ± 116.98 | 111.8 ± 135.93 | <0.001 |
| N-Ac-5-ASA | 871.1 ± 385.21 | 642.1 ± 534.46 | 0.001 |
| 4-ABA | 13.2 ± 6.76 | 12.1 ± 8.61 | 0.279 |
| N-Ac-4-ABA | 42.4 ± 18.57 | 42.7 ± 27.96 | 0.609 |
| $AUC_{last}$ (ng·hr/mL) | | | |
| Balsalazide | 1353.9 ± 726.63 | 1522.6 ± 1006.20 | 0.193 |
| 5-ASA | 2587.3 ± 1463.56 | 2096.4 ± 2577.31 | 0.019 |
| N-Ac-5-ASA | 17859.8 ± 8145.31 | 17727.2 ± 13720.51 | 0.173 |
| 4-ABA | 288.0 ± 158.11 | 302.0 ± 262.07 | 0.378 |
| N-Ac-4-ABA | 1110.3 ± 436.58 | 1127.8 ± 778.07 | 0.404 |
| $T_{max}$ (h) | | | |
| Balsalazide | 0.8 ± 0.85 | 1.2 ± 1.11 | 0.068 |
| 5-ASA | 8.2 ± 1.98 | 22.0 ± 8.23 | <0.001 |
| N-Ac-5-ASA | 9.9 ± 2.49 | 20.2 ± 8.94 | <0.001 |
| 4-ABA | 12.7 ± 9.46 | 24.0 ± 8.51 | 0.003 |
| N-Ac-4-ABA | 20.5 ± 12.30 | 25.4 ± 7.41 | 0.085 |

[a] p value derived from Dunnett's test for multiple comparisons for log-transformed $C_{max}$ and $AUC_{last}$, and from Wilcoxon Rank-Sum test for observed values of $T_{max}$.

When dosed with a standard high fat meal, significant decreases were seen in the systemic levels of 5-ASA and NASA as measured by the $C_{max}$ parameter. A significant decrease was also observed in the systemic levels of 5-ASA as measured by $AUC_{last}$. Dosing with food therefore allows for less systemic exposure to the total of the mesalamine products 5-ASA and NASA, as is preferred for reducing the side effect profile of balsalazide. Table 1 also shows that dosing with food significantly delays the $T_{max}$, which is a measure of the time to appearance in plasma of 5-ASA (8.2 hr vs 22.0 hr) and NASA (9.9 hr vs 20.2 hr). This delay is indicative of a slower transit of the drug through the GI tract.

The data from the food effect study is also displayed in Table 2 as a ratio of the values observed for the fed state divided by those observed for the fasted state. The data displayed in Table 2 also include data derived from a study (BZPK1002) using a 1100 mg tablet formulation of balsalazide. The magnitude of the decrease in $C_{max}$ and $AUC_{last}$ can clearly be seen in this data display as well as the reproducible nature of the experiment. The data also show that the effect of food on plasma 5-ASA and NASA derived from balsalazide is independent of the formulation employed.

TABLE 2

Ratios and 90% Confidence Intervals of Different Treatments for Plasma Pharmacokinetics for Balsalazide, 5-ASA, and N-Ac-5-ASA

| | Treatment B/A[a] | | |
|---|---|---|---|
| | Ratio | Lower Limit | Upper Limit |
| 750 mg Capsule $C_{max}$[b] | | | |
| Balsalazide | 0.791 | 0.597 | 1.048 |
| 5-ASA | 0.427 | 0.294 | 0.620 |
| N-Ac-5-ASA | 0.639 | 0.505 | 0.809 |
| $AUC_{last}$[b] | | | |

TABLE 2-continued

Ratios and 90% Confidence Intervals of Different Treatments for
Plasma Pharmacokinetics for Balsalazide, 5-ASA, and N-Ac-5-ASA

| | Treatment B/A[a] | | |
|---|---|---|---|
| | Ratio | Lower Limit | Upper Limit |
| Balsalazide | 1.146 | 0.971 | 1.352 |
| 5-ASA | 0.589 | 0.401 | 0.864 |
| N-Ac-5-ASA | 0.819 | 0.649 | 1.034 |
| 1100 mg Tablet $C_{max}^{b}$ | | | |
| Balsalazide | 0.564 | 0.497 | 0.641 |
| 5-ASA | 0.343 | 0.292 | 0.404 |
| N-Ac-5-ASA | 0.525 | 0.473 | 0.582 |
| $AUC_{last}^{b}$ | | | |
| Balsalazide | 0.913 | 0.819 | 1.017 |
| 5-ASA | 0.524 | 0.465 | 0.590 |
| N-Ac-5-ASA | 0.810 | 0.750 | 0.866 |

[a]Treatment A = Fasted; Treatment B = High Fat Breakfast;
[b]Ratio estimates and 90% CIs from ANOVA fitting mixed model using log-transformed values: log (parameter) = study group period treatment subject (study group), where subject (study group) was a random effect, comparing high-fat diet vs. fasting, The observed prolongation of $T_{max}$ and therefore slower transit through the GI could result in an increased exposure of the colonic mucosa to the therapeutically active 5-ASA. If this occurred, one would expect a change in the ratio of NASA to ASA as seen in the plasma. To test this possibility the plasma ratios of NASA to 5-ASA were examined. These data are shown in FIG. 2.

Figure 2:
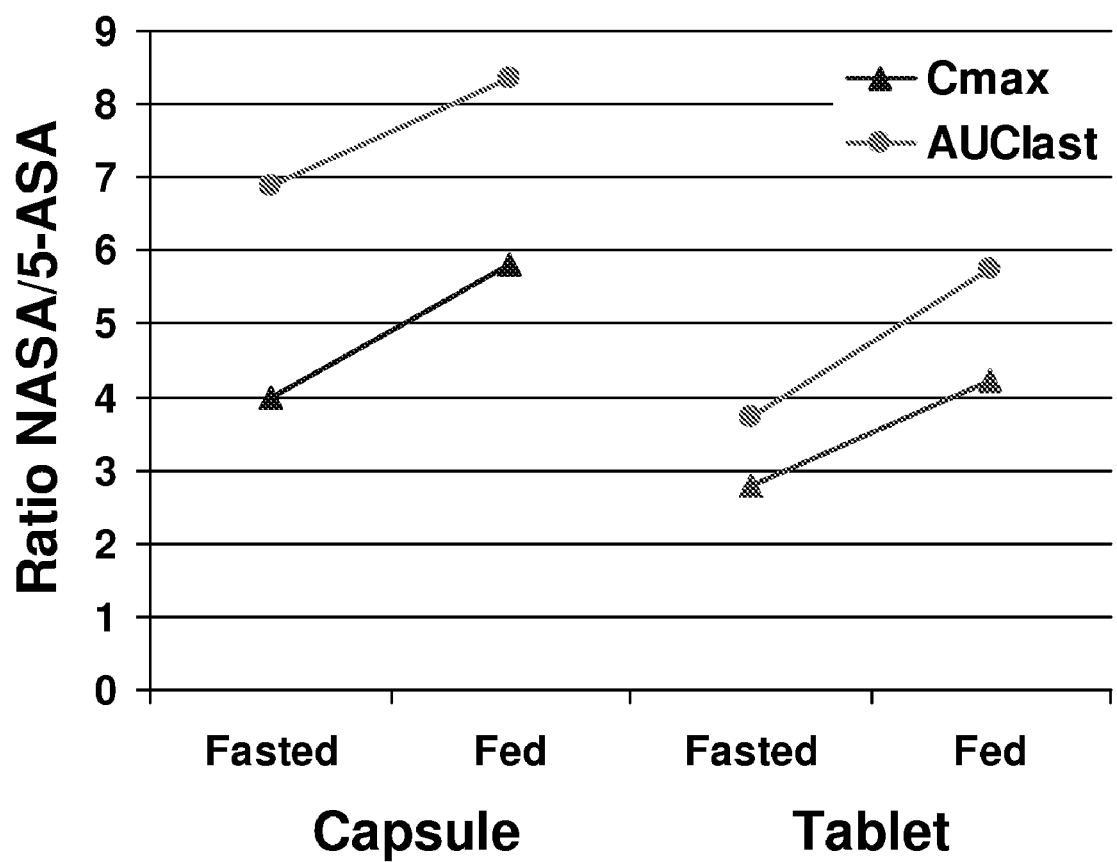
FIG. 2 shows the ratio of plasma NASA to 5-ASA for $C_{max}$ and $AUC_{last}$ in the fasted and fed state.

The data of FIG. 2 show that the systemic ratio of NASA to 5-ASA increases when balsalazide is given to subjects that have been fed compared to subjects that have fasted. It is therefore concluded that administering balsalazide to subjects in the presence of food prolongs the transit of 5-ASA in the colon and allows a greater conversion of 5-ASA to NASA. The increased contact of 5-ASA with the colonic mucosa can increase efficacy of the drug. The lower systemic 5-ASA levels can decrease the side effect profile. Therefore dosing UC subjects with balsalazide concurrently with food is a preferred but unexpected dose regimen.

What is claimed is:

1. A method of treating a gastrointestinal disorder comprising: administering to a subject in need of treatment a therapeutically effective amount of balsalazide with food, wherein said administering with food comprises administering balsalazide within 15 minutes after eating a meal, and wherein the administration results in an increase in the bioavailability of balsalazide and metabolites 5-aminosalicylic acid (5-ASA) and N-acetyl-5-ASA (NASA) to the colon of the subject as compared to administration of balsalazide in a fasted state.

2. The method according to claim 1, wherein the balsalazide is administered from a container with printed labeling advising that administration with food results in one or more of a delay of the transit of the balsalazide, 5-ASA or NASA in the colon of a subject; a decrease in the systemic level of one or more of 5-ASA or NASA in a subject; decrease in the maximal plasma concentration ($C_{max}$) of one or more of balsalazide, 5-ASA or NASA in a subject; delaying $T_{max}$ of one or more of balsalazide, 5-ASA or NASA in a subject; decreasing the extent of absorption ($AUC_{last}$) of one or more of 5-ASA or NASA in a subject; increasing conversion of balsalazide to 5-ASA and 5-ASA to NASA in a subject or increasing the systemic ratio of NASA to 5-ASA in a subject.

3. The method of claim 1, further comprising informing the subject that the administration of a therapeutically effective amount of balsalazide in a pharmaceutical composition with food results in an increase in the bioavailability of balsalazide and metabolites 5-ASA and NASA.

4. The method claim 1, wherein the therapeutically effective amount comprises from between about 6.25 mg to about 14000 mg/day; or from between about 750 mg to about 6750 mg/day; or from between about 1100 mg to about 13200 mg/day.

5. The method of claim 1, wherein the therapeutically effective amount is a dosage regimen of three capsules of the formulation three times each day, wherein each capsule comprises about 750 mg of balsalazide.

6. The method of claim 1, wherein the therapeutically effective amount is a dosage regimen of three tablets of the formulation two times each day, wherein each tablet comprises about 1100 mg of balsalazide.

7. The method of claim 1, wherein the therapeutically effective amount is a dosage regimen of one capsule three times each day, wherein each capsule comprises about 750 mg of balsalazide.

8. The method of claim 1, wherein the food comprises one or more of applesauce or a high-fat meal.

9. The method of claim 1, wherein the gastrointestinal disorder comprises one or more of mild to moderately active ulcerative colitis, radiation proctosigmoiditis, and colon cancer.

* * * * *